United States Patent
Jacob

(10) Patent No.: US 11,464,286 B2
(45) Date of Patent: Oct. 11, 2022

(54) INTERNET CONNECTED ADJUSTABLE STRUCTURAL SUPPORT AND CUSHIONING SYSTEM FOR FOOTWEAR

(71) Applicant: Dennis George Jacob, Horseheads, NY (US)

(72) Inventor: Dennis George Jacob, Horseheads, NY (US)

(*) Notice: Subject to any disclaimer, the term of this patent is extended or adjusted under 35 U.S.C. 154(b) by 116 days.

(21) Appl. No.: 16/712,443

(22) Filed: Dec. 12, 2019

(65) Prior Publication Data

US 2020/0297072 A1  Sep. 24, 2020

Related U.S. Application Data

(60) Provisional application No. 62/821,196, filed on Mar. 20, 2019.

(51) Int. Cl.
*A43B 13/20* (2006.01)
*A43B 3/34* (2022.01)

(52) U.S. Cl.
CPC .............. *A43B 13/20* (2013.01); *A43B 3/34* (2022.01)

(58) Field of Classification Search
CPC ..... A43B 13/20; A43B 3/0005; A43B 13/203; A43B 5/0407
See application file for complete search history.

(56) References Cited

U.S. PATENT DOCUMENTS

| | | | | |
|---|---|---|---|---|
| 5,025,575 A * | 6/1991 | Lakic | ............... | A43B 13/203 36/44 |
| 5,199,191 A * | 4/1993 | Moumdjian | ......... | A43B 13/203 36/25 R |
| 5,655,316 A * | 8/1997 | Huang | ............... | A43B 3/00 36/132 |
| 5,813,142 A * | 9/1998 | Demon | ............... | A43B 3/0005 36/28 |
| 6,510,624 B1 * | 1/2003 | Lakic | ............... | A43B 17/035 36/28 |
| 7,448,150 B1 * | 11/2008 | Davis | ............... | A43B 13/203 36/153 |
| 2003/0009913 A1 * | 1/2003 | Potter | ............... | A43B 3/0005 36/29 |
| 2007/0051018 A1 * | 3/2007 | Issler | ............... | A43B 9/02 36/29 |
| 2007/0129907 A1 * | 6/2007 | Demon | ............... | A43B 3/0005 702/127 |
| 2009/0273311 A1 * | 11/2009 | Beers | ............... | A43B 11/00 320/108 |
| 2014/0165427 A1 * | 6/2014 | Molyneux | ............... | A43B 21/26 36/102 |
| 2015/0150337 A1 * | 6/2015 | Zsolcsak | ............... | A43B 7/1445 219/211 |
| 2015/0189944 A1 * | 7/2015 | Ellis | ............... | A43B 23/0285 36/87 |
| 2015/0305436 A1 * | 10/2015 | Doyle | ............... | A43B 13/203 36/43 |

(Continued)

*Primary Examiner* — Jameson D Collier
*Assistant Examiner* — Matthew R Marchewka
(74) *Attorney, Agent, or Firm* — Brown & Michaels, PC

(57) ABSTRACT

An apparatus for a shoe sole with an air pump for adjusting pressure levels in air chambers distributed throughout the sole, and a battery. A sole system cloud based application remotely connects to and adjusts the air chambers according to user preferences.

11 Claims, 8 Drawing Sheets

(56) References Cited

U.S. PATENT DOCUMENTS

| | | | |
|---|---|---|---|
| 2016/0174657 A1* | 6/2016 | Fox-Mudge | A43B 13/183 |
| | | | 36/29 |
| 2017/0265563 A1* | 9/2017 | Ma | A43B 3/0005 |
| 2018/0008005 A1* | 1/2018 | Compton | A43B 13/203 |
| 2018/0132566 A1* | 5/2018 | Rosenblatt | A43B 17/026 |
| 2018/0344210 A1* | 12/2018 | Pestl | A61B 5/6807 |
| 2019/0000183 A1* | 1/2019 | Mou | A43B 3/0015 |
| 2019/0373984 A1* | 12/2019 | Wijesundara | A43B 7/1475 |
| 2021/0145622 A1* | 5/2021 | Riffel | A43B 3/00 |

\* cited by examiner

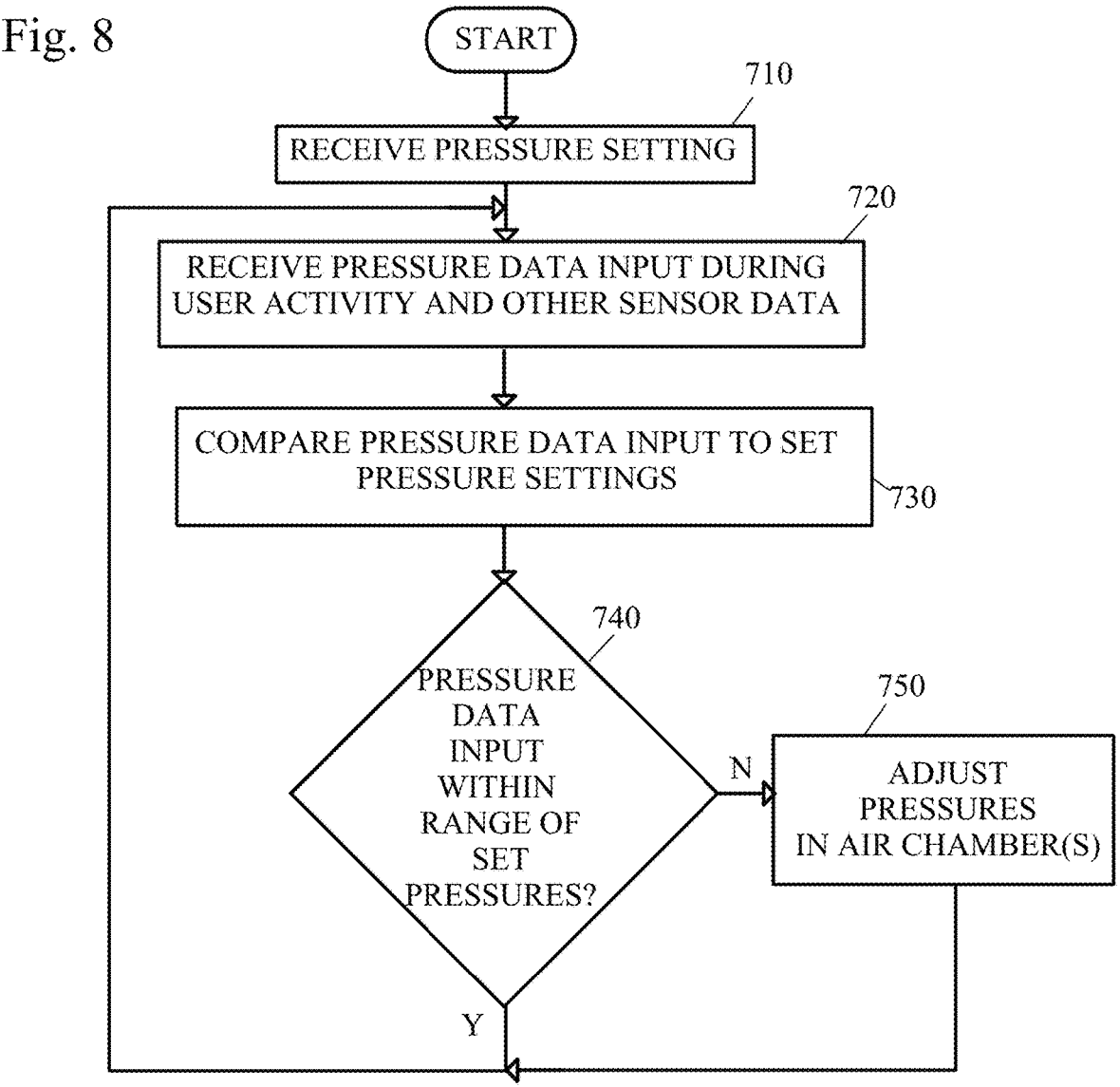

INTERNET CONNECTED ADJUSTABLE STRUCTURAL SUPPORT AND CUSHIONING SYSTEM FOR FOOTWEAR

REFERENCE TO RELATED APPLICATIONS

This application claims one or more inventions which were disclosed in Provisional Application No. 62/821,196, filed Mar. 20, 2019, entitled "INTERNET CONNECTED ADJUSTABLE STRUCTURAL SUPPORT AND CUSHIONING SYSTEM FOR FOOTWEAR". The benefit under 35 USC § 119(e) of the United States provisional application is hereby claimed, and the aforementioned application is hereby incorporated herein by reference.

BACKGROUND OF THE INVENTION

Field of the Invention

The invention pertains to the field of footwear. More particularly, the invention pertains to an internet connected adjustable structural support and cushioning system for footwear.

Description of Related Art

Generally, there are three types of foot arches associated with the human foot. Many people encounter pain in their feet, bone spurs, and other problems based upon the arch of their foot being high, medium or low. Some people have low arches which are characterized by an arch that sits low to the ground. Low arches are often biomechanically imbalanced and cause susceptibility to common foot problems such as heel pain, arch pain and plantar fasciitis. Other people have medium arches which are characterized as a well-defined arch. Medium arches are often biomechanically efficient but still can be susceptible to common foot problems such as heel pain or ball-of-foot discomfort. Yet another segment of the population has high arches that are characterized as arches that sit high from the ground. High arches have less surface area for absorbing impact from when walking or running or during sports which causes excessive pressure on the rear foot and forefoot areas. This can increase susceptibility to foot conditions such as heel pain, ball-of-foot pain or plantar fasciitis. Still, most arches fall somewhere in between these three categories, with very few people having an arch that can be purely characterized as low, medium, or high.

Generally, many people who suffer from foot problems related to their arch seek to remedy the problem with insoles. Insoles are expensive and the process for fitting insoles is inexact because every foot is unique.

SUMMARY OF THE INVENTION

An internet-enabled sole system, which allows for a fully adjustable support system through custom pressurized air chambers to provide comfort to the foot of the user, is disclosed herein. The sole system is embedded within the shoes through modification of the traditional insole, midsole and outsole sections. In a preferred embodiment, the sole system includes an embedded air pump, compressor, or inflator/deflator operably connected to three air chambers for adjusting the level of air in each chamber through commands received from an application on a computing device or from any Internet connected device. The insole section consists of three separate chambers—a forefoot chamber, a heel chamber and an arch chamber. By modifying the insole, midsole and outsole sections of the sole, through one or more associated chambers, the support to a user can be varied. The forefoot and heel chambers can expand and contract as needed to provide either more or less support to the user. The arch chamber changes to provide support to the user based upon the needs of the user.

In another embodiment, the sole system includes an external air inlet, adapted to engage with an external air pump, external compressor, or an external inflator/deflator, operably connected to a plurality of air chambers in the sole of the shoe for pressurizing and adjusting the level of air in each chamber through an action. The embedded air pump, compressor, or inflator/deflator is operably connected to the plurality of air chambers for adjusting the level of air in each chamber through commands received from an application on a computing device or from any Internet connected device. The insole section consists of at least four separate chambers. Each chamber of the plurality of chambers located throughout the sole can individually expand and contract as needed to provide more or less support to the user. The individual chambers can change to provide support to the user based upon the needs of the user.

In another embodiment, the sole system involves an embedded air pump, compressor, or inflator/deflator operably connected to a single air chamber for adjusting the level of air through commands received from an application on a computing device or from any Internet connected device.

In an additional embodiment, the sole system includes an external air inlet, adapted to engage with an external air pump, an external compressor, or an external inflator/deflator, and is operably connected to a single air chamber for pressurizing and adjusting the level of air in each chamber of the sole system.

If the consumer is flat-footed, at least one chamber of the sole increases the pressure within the chamber to raise up, or expand and form a firm support. If the user is high-arched, at least one chamber decreases the pressure present within the chamber to soften and contract. Through a combination of the chambers in the sole, the user is able to achieve support and comfort.

The Internet of Things (IoT) capacity of the sole system allows for several different modes of operation. The soles allow remote access by another user, such as a medical professional to check and/or monitor the settings of the shoes of a user to ensure maximum benefit. The user can monitor their own comfort level and alter the support provided through an application connected to the soles. Machine learning can be utilized to find the optimum levels for a user by applying data collected over a period of time. The sole system obviates the need for special insoles and allows for customization of the support provided to a user

BRIEF DESCRIPTION OF THE DRAWING

FIG. 8 shows a flow diagram of a method of adjusting a shoe sole support system through custom pressurized air chambers to provide comfort to the foot of the user.

DETAILED DESCRIPTION OF THE INVENTION

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

Figure 2:
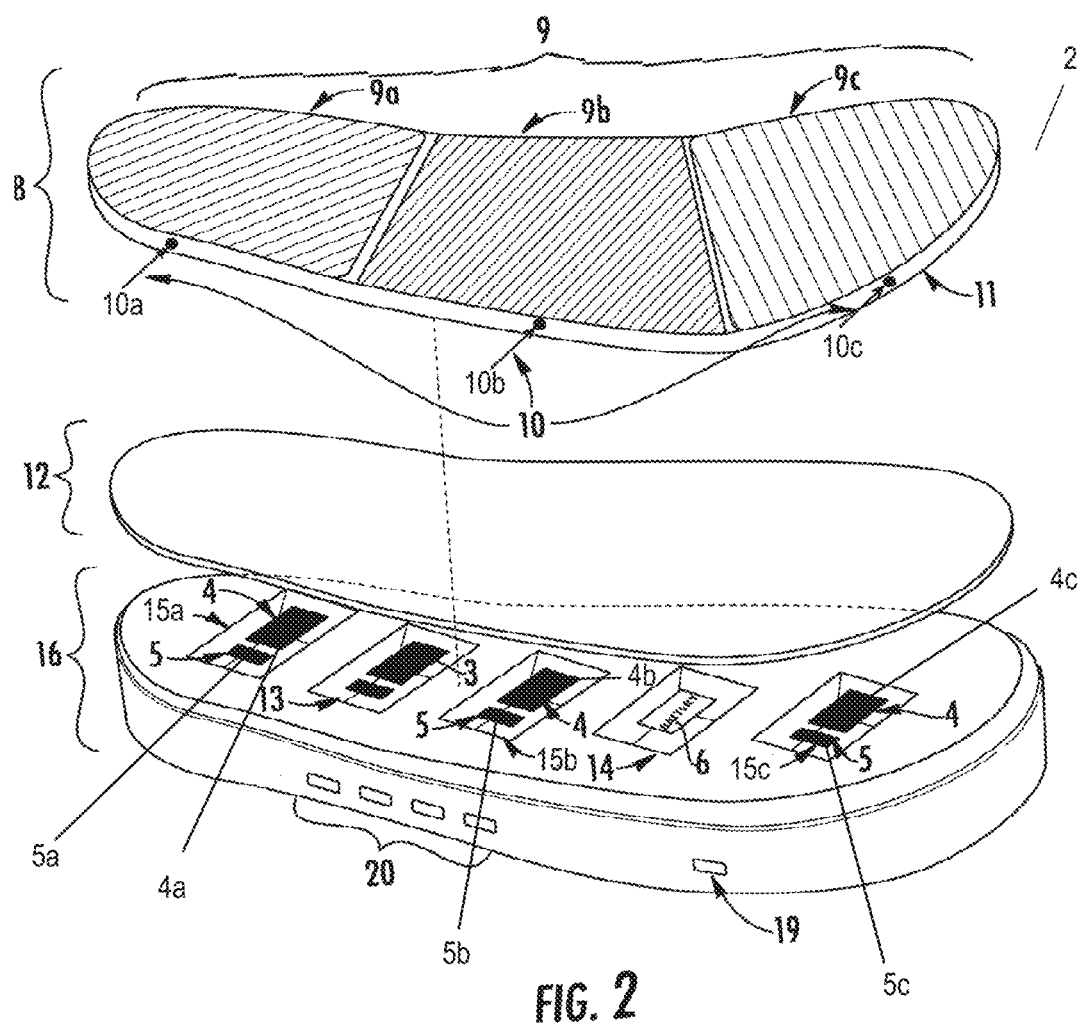
FIG. 2 shows the internal details of a shoe sole, according to an embodiment of the invention.

FIG. 2 shows the internal details of a shoe sole, according to the invention. A sole system 2 is attached to the upper portion 1 of a shoe. The upper portion 1 of the shoe can consist of one or more of the following materials: synthetic leather, real leather (full-grain, top-grain, suede, genuine or bonded), nylon fabric, canvas, synthetic fuse, carbon fiber, fully knit upper, cloth, carbon based polymers, or animal skin. Sole system 2 can be constituted with one or more of the following materials, but not limited to: carbon fiber, any metal/alloy, Ethylene Vinyl Acetate (EVA), any synthetic foam, carbon-based polymers, composite materials, vulcanized/normal rubber, or silicone. The sole system 2 preferably has an insole 8, midsole cover layer 12, and an outsole component layer 16.

Insole 8 preferably includes an air chamber 9 present within a carbon fiber based member 11. In this embodiment, air chamber 9 is split into three chambers, a forefoot chamber 9c at a first anterior end, a medial arch chamber 9b and a heel chamber 9a at a posterior end within the carbon fiber based member 11. Each of the air chambers 9a-9c are individually adjustable and customizable. The forefoot chamber 9c, the heel chamber 9a and the arch chamber 9b each contain a chamber inlet/outlet 10a-10c within the carbon fiber member 11 for receiving and dispensing air. Each chamber inlet/outlet 10a-10c provides controlled inflation from an embedded air pump or compressor with an inflator/deflator 4 to the air chambers 9a-9c. The inflator/deflator 4c, located in upper portion 1 or the forefoot chamber 9c at a first anterior end, is operably connected to the chamber inlet/outlet 10a-10c. Air chamber 9 is preferably suited for cumulative pressure levels in the range of 5 to 100 psi (pounds per square inch), where the heel chamber 9a has a pressure of 30 to 50 psi and the arch chamber 9b and forefeet chamber 9c each has a pressure of 20 to 40 psi.

Midsole cover layer 12 is located between insole 8 and outer component layer 16 acting as an outsole. Midsole 12 is ideally made of waterproof, moisture wicking fiber to protect the battery compartment 14 containing one or more rechargeable or non-rechargeable batteries 6 from water and other elements.

Outer component layer 16 houses the electrical and electronic components of sole system 2 embedded in individual secure compartments from the anterior portion of the sole to the posterior portion of the sole system 2. The outer component layer 16 also includes a wireless connectivity indicator 19 and a charge indicator 20. The wireless indicator 19 displays the wireless Internet or wireless connection status of sole system 2. The charge indicator 20 provides a visual status of the available charge or charging progress of battery 6. These indicators also can have other manifestations for enhancing the aesthetics of the shoes.

In the anterior portion of the sole system 2, the medial portion of the sole system 2 and the posterior of the sole system 2 are three separate compartments 15 that each house air pump or compressor with an inflator/deflator 4a-4c for each of the chambers 9a-9c and at least a pressure sensor 5. The pressure sensors 5a-5c sense pressure data associated with the air present in each of the chambers 9a-9c. The pressure sensor 5 can additionally measure the pressure associated with a user's foot relative to the forefoot chamber 9c, the medial arch chamber 9b and the heel chamber 9a during specific activities by the user's foot.

The anterior portion of the outer component layer 16 and the first compartment 15c is aligned with the forefoot chamber 9c, the medial portion of the outer component layer 16 and the second compartment 15b is aligned with medial arch chamber 9b, and the posterior portion of the outer component layer 16 and the third compartment 15a is aligned with the heel chamber 9a. Between the first compartment 15c, at the anterior portion, and the second compartment 15b, at the medial portion of the sole, is a battery compartment 14. The battery compartment 14 contains one or more batteries 6. Between the third compartment 15a at the posterior portion and the second compartment 15b at medial portion of the sole system 2 is a processor compartment 13. Heat radiating from the battery 6 can be used to provide heat through the sole to the user's foot.

The processor compartment 13 includes an embedded processor 3. Embedded processor 3 preferably includes software, for example a sole system program 18 for controlling the air pump or compressor with an inflator/deflator 4 to maintain a desired air pressure in the air chambers 9a-9c. The sole system program 18 is discussed in further detail below. The embedded processor can also contain associated circuitry to convert induced alternating current to a direct current (DC) from a metallic induction coil 23 (see FIG. 3) for the electromagnetic charging of a battery 6.

Figure 3:
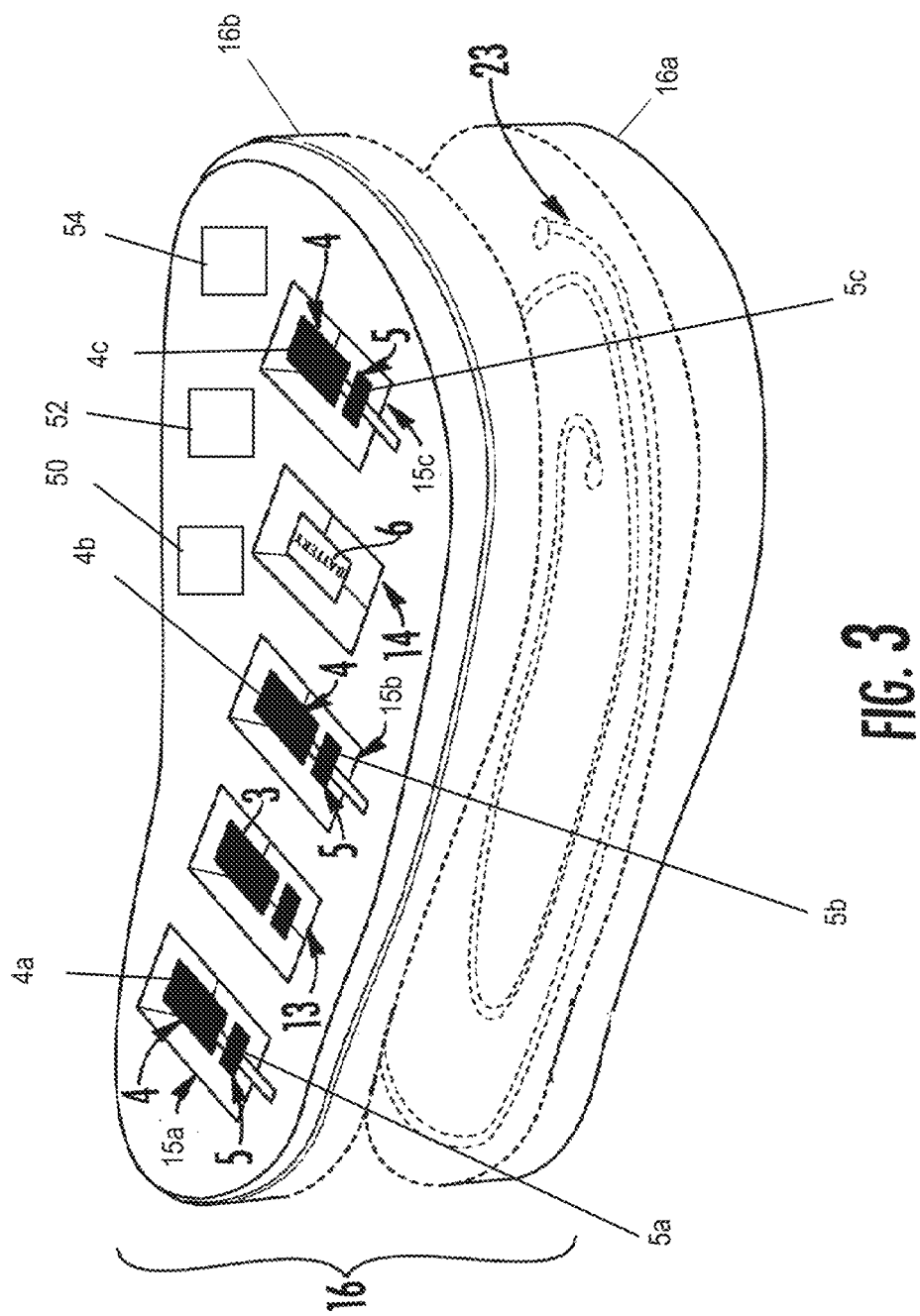
FIG. 3 shows a dissected view of the bottom portion of the shoe sole as illustrated in FIG. 2, according to an embodiment of the invention.

FIG. 3 shows a dissected view of the outer component layer 16 of the shoe sole as illustrated in FIG. 2, according to the invention. Outer component layer 16 of sole system 2 has a top portion 16b and a bottom portion 16a. The bottom portion 16a contains a charging coil 23 which to enable wireless charging of battery 6. Although sole system 2 uses wireless or inductive charging, as indicated, it is well known to a person of skill in the art that sole system 2 is capable of charging battery 6 with a direct plug-in power source or utilizing a non-rechargeable, replaceable, battery as a power source.

Figure 4:
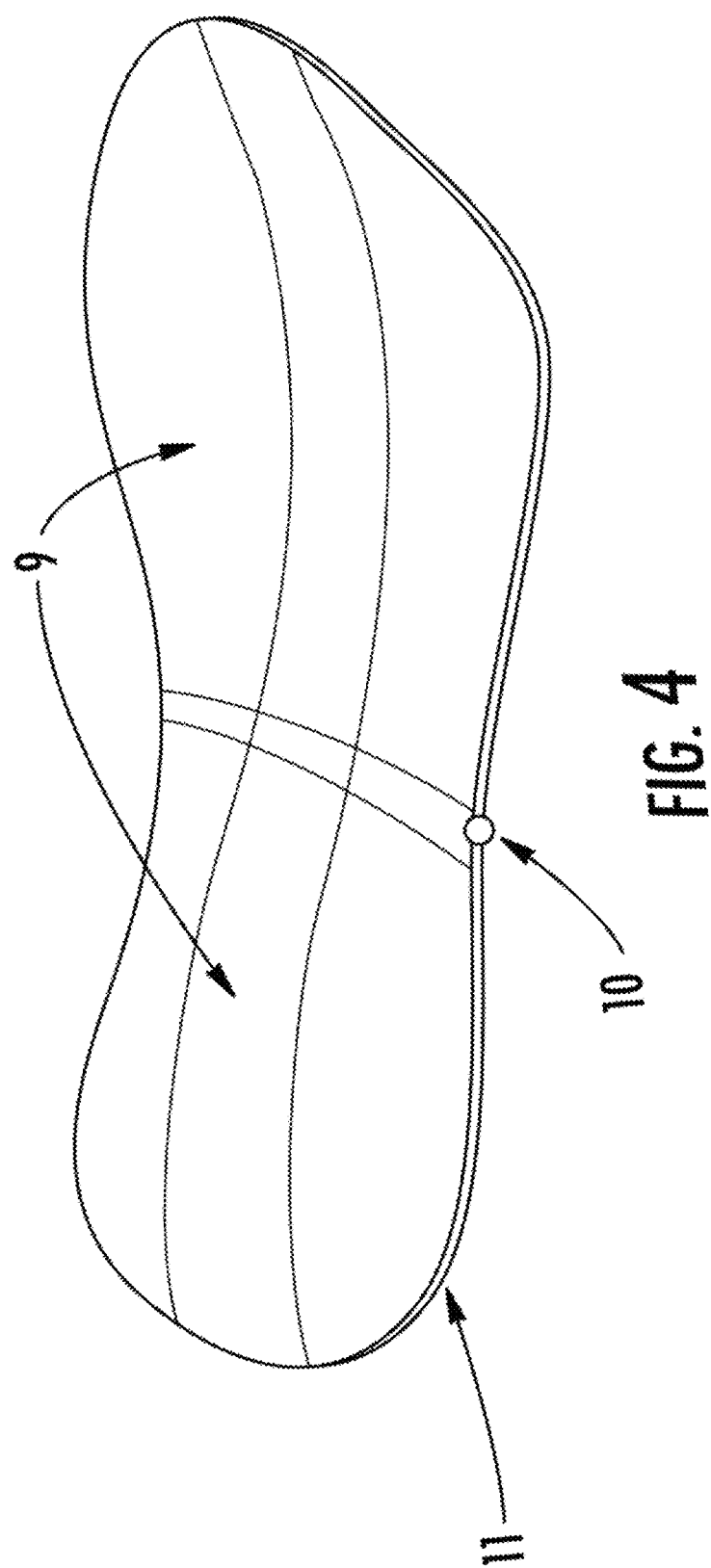
FIG. 4 shows a shoe sole configuration, according to one embodiment of the invention.

FIG. 4 shows a shoe sole configuration, according to one embodiment of the invention, in which a single air chamber is present. In this embodiment, the insole 8 of the sole system 2 contains air chamber 9 with a chamber inlet 10 within a carbon fiber member 11.

Figure 5:
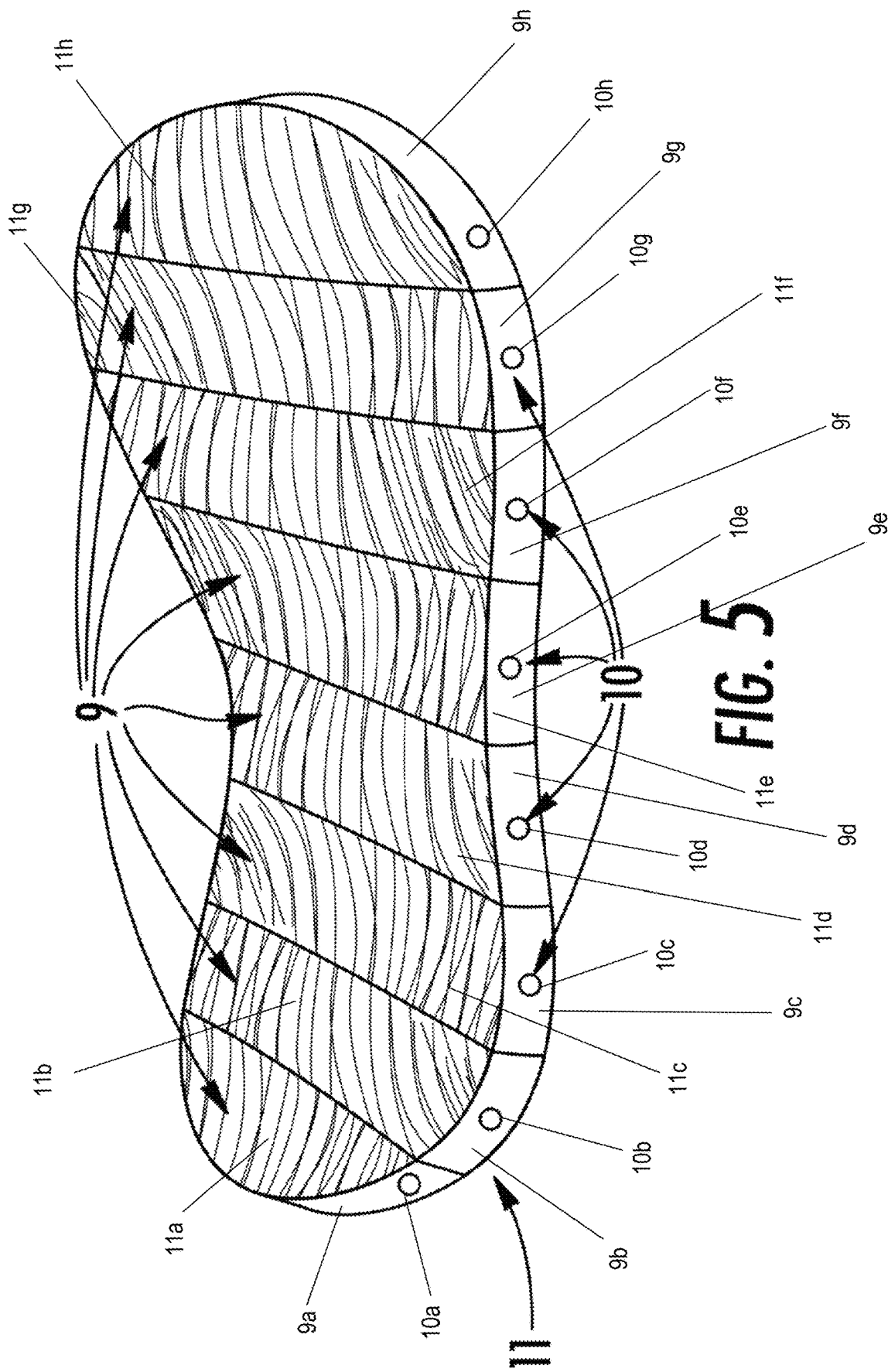
FIG. 5 shows a shoe sole configuration, according to another embodiment of the invention.

FIG. 5 shows a shoe sole configuration, according to another embodiment of the invention. In this embodiment, multiple air chambers are present. Insole 8 has a plurality of individual air chambers 9a-9h (not shown) present within the carbon fiber member 11, with each individual air chamber 9a-9h (not shown) containing its own chamber inlet/outlet 10a-10h, within each carbon fiber portion 11a-11h of the carbon fiber member. Having a plurality of individual air chambers 9a-9h (not shown) provides the user with the ability to fine tune and adjust the pressure across multiple segments of their foot. While multiple air chambers are shown, the number of air chambers is not limited to the configuration or number of air chambers shown in the Figures.

Figure 6:
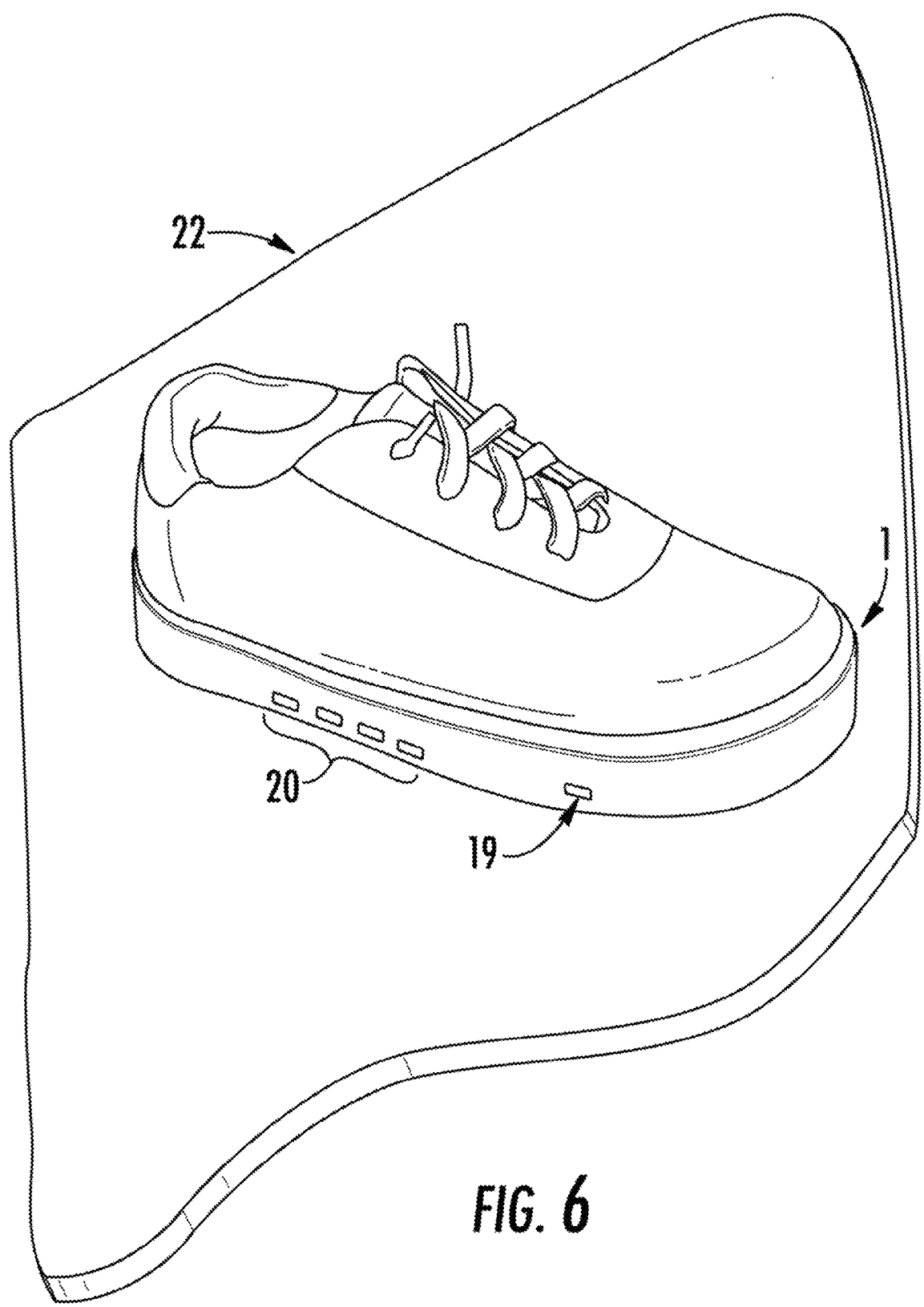
FIG. 6 shows an example of the shoe sole in charging mode, according to an embodiment of the invention.

FIG. 6 shows an example of the shoe sole in charging mode, according to one embodiment of the invention. In this embodiment, a wireless charging mat 22 includes an induction coil (not shown) and receives power from a direct plug-in power source and the wireless charging mat 22 utilizes the induction coil to create an alternating electromagnetic field from within the charging mat 22 and the metallic charging coil 23 takes the power from the electromagnetic field and converts it back into electric current to electromagnetically charge the battery 6 of sole system 2.

Figure 7:
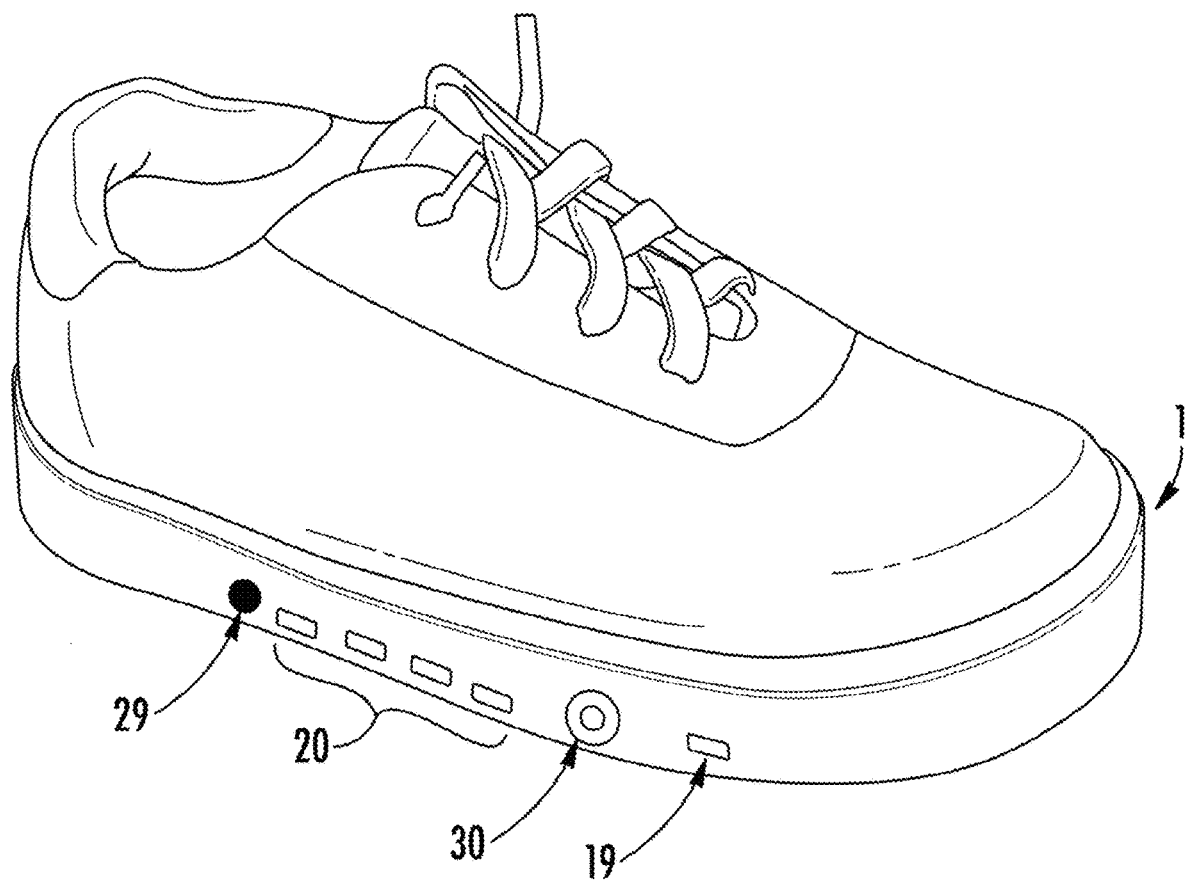
FIG. 7 shows a shoe sole configuration, according to an additional embodiment of the invention.

FIG. 7 shows a shoe sole configuration, according to another embodiment of the invention. In this embodiment, the sole system 2 includes an electronic switch 29, and an external air inlet 30.

The electronic switch 29 is a button, toggle switch, miniature lever, or other switch as is known in the art. The electronic switch 29 is capable of performing at least one of three actions as initiated by a user—initiating a powering up process, where the sole system 2 is activated or initiated, a powering down process, where the sole system 2 is deactivated or turned off, or initiating a resetting process of the sole system through a prolonged action, such as a compression of the electronic switch 29 for at least 3 seconds by the user.

The external air inlet 30 is an external port that is directly connected to one or more air chambers 9 of the sole system 2. The external air inlet 30 is adapted to receive and couple with an external air pump, external compressor, or an external inflator/deflator. Embedded processor 3, through the sole system program 18 can control the amount of air, and air pressure received by the external air inlet 30 through sole system program 18 setting a minimum level of air and air pressure, a maximum level of air and air pressure, and a range of air and air pressure according to user preferences.

In another embodiment, the wireless charging mat 22 includes an attached external pump, or compressor with a deflator, to couple with the external air inlet 30. In an example, sole system 2 could automatically externally adjust the air pressure to a desired value through a direct attachment to the inlet for external air inlet 30, in one or more air chambers 9, when the sole system 2 physically interfaces with the wireless charging mat 22.

Figure 1:
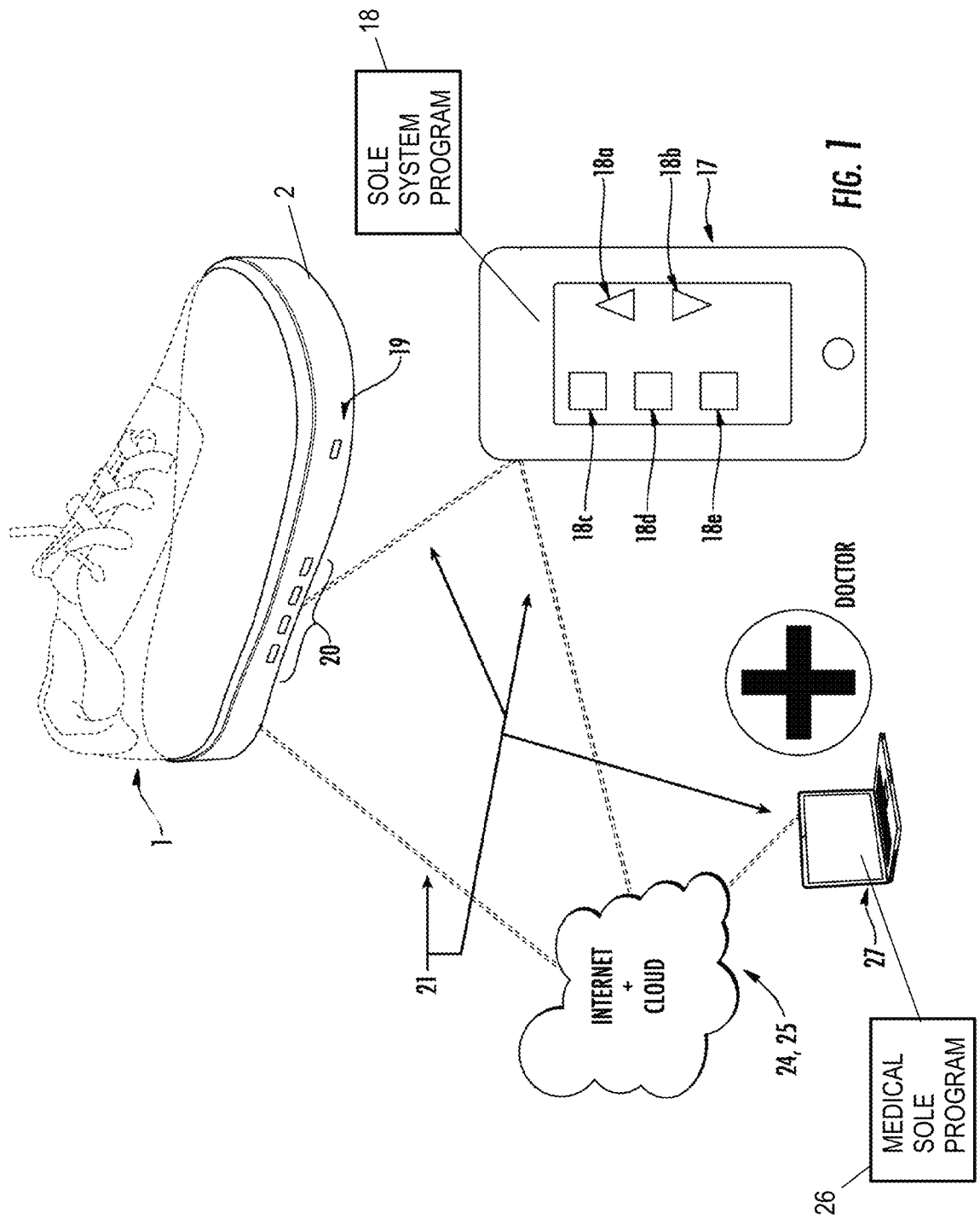
FIG. 1 shows a data processing environment, according to one embodiment of the invention.

FIG. 1 shows the data processing environment of the invention.

The embedded processor 3 of the sole system 2 contains software, for example sole system program 18, for controlling the air pump or compressor with an inflator/deflator 4 to maintain a desired air pressure in the air chambers 9. The sole system program 18 communicates with the embedded processor 3 via short range communication or through the Internet and/or cloud 24, 25. The sole system program 18 additionally can be present on a remote computing device 27. The remote computing device 27 additional contains one or more processors and associated memories. The sole system program 18 allows for alteration of set points associated with the air chambers 9 of the sole system 2 from a remotely connected device.

Sole system 2 captures real time data from the air chambers 9 through pressure sensors 5 while a user is performing various activities wearing the sole system 2, such as walking, hiking, running, playing, etc. Pressures being set in the air chambers 9 are monitored by pressure sensors 5 that can capture alterations in the pressure received on the air chambers 9 by the user's foot. Additional sensors can be present within the outsole component layer 16 and can include one or more of the following sensors: a heart rate sensor 50, a blood pressure sensor 52, or a motion sensor 54. The motion sensor 54 can be connected to and may trigger activation of an embedded miniature camera for capturing visual sensory data associated with the user of the sole system 2. The visual sensory data can be provided to a Global Positioning System (GPS) of the embedded computer 3 to enhance machine learning based guidance for users.

Sole system 2 is wirelessly connected 21 to hand held device 17 and computing device 27 via network 24. Wireless connection could be any of, but not limited to, the following: Wi-Fi, 3G, 4G, LTE, 5G, BLUETOOTH® and/or any future wireless standard. The communication between the processor of the sole system and the processor of a remote computing device can take place wirelessly via short or long range communication protocols. Examples of short range communication protocols can include, but is not limited to: near-field communications (NFC), radio-frequency identification (RFID), infrared wireless (IR), BLUETOOTH® or any other or future communication protocols.

Hand held device 17 may be a mobile device, smartphone, tablet, smartwatch, or any other device with a user interface (not pictured) which accepts commands from a user associated with air provided to or released from the air chambers 9 and a sole system program 18. The user interface may be, but is not limited to, a command line interface, a graphical user interface (GUI), a natural user interface (NUI) or a touch user interface (TUI). The sole system program 18 preferably includes a user interface with selectors 18c, 18d, 18e for specific pressure chambers 9 as well as selectors 18a, 18b for increasing or decreasing the pressure in the pressure chambers 9.

Computing device 27 may be a computer with medical sole system program 26. Medical sole system program 26 operates similarly to sole system program 18 on the handheld device 17 and preferably includes Health Insurance Portability and Accountability Act (HIPPA) compliant communication protocols for communicating with a medical professional. Medical sole system program 26 enables a medical professional to monitor step and gait performance regularly, and make changes remotely to the support provided to the user. In addition, the medical professional can quantify comfort in terms of pressure relative to the chambers 9 of the sole system 2, rather than relying on in-person communications. Network 24 may be a wireless communication link or any wireless connection to the Internet.

FIG. 8 shows a flow diagram of method of adjusting a shoe sole support system through custom pressurized air chambers to provide comfort to the foot of the user.

In one embodiment, pressure and comfort data collected from sole system 2 is remitted to a cloud based server over a time period to determine settings for a user through advanced data analytics techniques or a neural network.

In another embodiment, medical sole system program 26, on computing device 27 is capable of receiving, storing, and sending user data to one or more servers (not pictured). In an example, a medical professional could utilize historical data and advanced data analytics to provide suggestions for adjusting the comfort level of a user which is a patient. In this embodiment, the medical professional is treating an ailment of the user that may be impacted by the user's foot, posture or the way the user carries out an activity. The medical professional can work interactively with the sole system 2 to adjust the support and comfort level relative to specific parts of the user's foot. While a user (e.g. a secondary user) other than the user wearing the shoe is discussed as being a medical professional, the other user may be a trainer or other individual that not has a specific professional training, medical degree or license.

In a first step (step 710) a pressure setting is received by the medical sole system program 26. In an embodiment, a medical professional applies a pressure setting, received through medical sole system program 26 on computing device 27, as an initial pressure setting in one or more air chambers 9 based on a complaint from a user. In this embodiment, a user may have a complaint about pain in the heel area. The medical sole system program 26, can receive, via a user interface, a pressure setting from the medical profession, for example between 30-50 pounds per square inch (psi) in the heel area to reduce heel pressure and the corresponding impact force. Setting the pressure reduces load on the foot of a user, prolongs the amount of time from initial foot to ground contact until complete compression of the shoe of the user, and promotes distribution of the actual foot pressure on the shoe of the user.

In another embodiment, the medical sole system program 26, can receive, via a user interface, a pressure setting in one or more air chambers 9 based on an observed deficiency in the user's gait, or as a function of observing the manner in which the shoe of a user is worn down. In this embodiment, a medical professional may recognize a pattern of wear on the shoe that is symptomatic of over protonation in the gait of a user. The medical professional may adjust the one or more air chambers 9 in the heel of the shoe of the user to provide additional support to counter the over protonation.

In another embodiment, the medical sole system program 26, can receive, via a user interface, a pressure setting to compensate for under protonation by increasing the pressure in one or more air chambers 9 that correspond to the arch area in the shoe of a user.

In another embodiment, the medical sole system program 26, can receive, via a user interface, a pressure setting in one or more air chambers 9 located in the forefoot area in response to a user recovering from an injury to the area.

In a next step (step 720) the medical sole system program 26 receives a pressure data input during an activity by the user from the sole system 2, for example via the sole system program 18. In an embodiment, the pressure data input includes the pressure exerted by the user on a surface during an activity such as walking, running, jumping, or any other physical activity that causes the foot of the user to strike, or make contact with, the ground surface. In another embodiment, the pressure data input of a pressure input from an activity of the user, is automatically uploaded to, and accessible through, a web based service by the medical sole system program 26. The web based service utilizes the pressure data input received from the one or more pressure sensors 5 and other sensors in sole system 2. The pressure data input includes at least data related to the psi settings and the actual psi exerted by the user on the one or more air chambers 9 of the sole system 2.

In another embodiment, based on pressure data input and other sensor input from the sole system, the medical sole system program 26 is capable of determining the type of ground surface the shoe of sole system 2 of the user is in contact with based upon measurements associated with the pressure data input. In this embodiment, the medical sole system program 26 determines the type of ground surface that the user contacts as a function of the measurement of the duration of time from the initial sole system 2 to ground contact until complete compression of the air chambers 9 until release from the ground and decompression of the air chambers 9. A longer duration of time of compression of the air chambers 9 is associated with a viscous surface such as sand. Comparatively, a shorter duration of time of compression of the air chambers 9 is associated with a more elastic surface.

In another embodiment, the medical sole system program 26 is constantly receiving pressure data input, in real time, from the one or more pressure sensors 5. In this embodiment, the medical sole system program 26 constantly receives, and stores the pressure data received from the one or more pressure sensors 5 to the computing device 27 to establish data trends with respect to pressure data of the user. For example, a machine learning application may utilize the pressure data input received by the medical sole system program 26 to analyze trends with respect to the amount of pressure applied in a particular region of the foot. In this example, the pressure trends could be analyzed by a medical professional to determine that a user walks with a gait which indicates an injury that is unknown to the user. In another example, the pressure trends could be used by a medical professional to analyze and compare the amount of pressure applied to specific regions of the shoe of the user based on the type of shoe worn by the user.

In a further step (step 730) the medical sole system program 26 compares the pressure input data received from the sole system 2 being worn by the user or patient received in step 720, from the one or more pressure sensors 5 of one or more air chambers 9, to the initial pressure setting received from the medical professional in step 710. In an embodiment, a medical professional in step 710 initially sets the pressure of one or more air chambers 9, in the heel of a shoe of a user, to a range of 30-35 p.s.i. In this embodiment, the sole system program 18 of embedded processor 3 sensed pressures of 32 p.s.i. through the one of more air chambers 9 in the forefoot of shoe of the user, a pressure of 30.02 p.s.i. through the one of more air chambers 9 in the arch area of the shoe of the user, and a pressure of 32.299 p.s.i. in the one or more air chambers 9 located in the heel area of the shoe of the user.

In a decision step (step 740) the medical sole system program 26 determines whether the pressure data input during an activity of the user is within a range of the set pressures based on the air pressure set to cushion the user's foot. In an embodiment, the medical sole system program 26 determines whether the pressure data input, as received by the one of more pressure sensors 5, in the one or more air chambers 9 located in the forefoot area, arch area, and the heel area of the shoe of the user, is within a range of p.s.i. as received by the medical sole system program 26 as a function of an input received as set by the medical professional in step 710.

If the determined pressures are within the range of the set pressures (step 740 "YES"), then the medical sole system program 26 returns to a sentinel mode, and resumes constantly receiving pressure data from the user during an activity of step 720. A sentinel mode is a surveillance mode where the medical sole system program 26 passively receives, monitors, and stores the pressure data received. It should be noted that step 720 can be conducted in the sentinel mode. In an embodiment, the pressure data is uploaded to the aforementioned cloud based server.

If the determined pressures are not within the range of the set pressures (step 740 "NO"), then the medical sole system program 26 adjusts the pressures (step 750) by sending updated pressure settings to the sole system 2, for example via the sole system program 18 and the method returns to step 720.

In an embodiment, the medical sole system program 26 determines that the pressure data is 29.5 p.s.i. and not within the appropriate range 30-35 p.s.i., of pressure and automatically adjusts the pressure settings in one or more air chambers 9, according to the medical professional recommendations via the embedded processor 3, for example through sole system program 18. For example, if the data received indicates that the user is walking on the outside of their foot in their shoe, additional pressure may be provided to one or more air chambers 9 to provide further cushion or support to another portion of the foot.

In another example, the pressure data received indicated, as a function of brief pressure reading interval increases, by the one or more pressure sensors 5, in areas of the shoe that correspond to a gait pattern that is signature of the user running, then the pressure settings are applied to be consistent within the appropriate range, 30-35 p.s.i. to aid in reducing heel pain in which the user experiences based on over protonation.

In another example, the medical sole system 26 may adjust the pressure in one or more air chambers 9 as a function of the type of surface the sole system 2 of user is determined to be situated upon. In this example, a user may be running on an elastic surface that is bouncy and requires less pressure in the heel are of air chambers 9. The medical sole system program 26 automatically adjusts the pressure in the heel area of air chambers 9 by reducing the p.s.i. as a function activating the inflator/deflator 4, through embedded processor 3 of the sole system 2, to decrease the pressure in this area.

After adjustments are made by the medical sole system program 26, to the one or more air chambers 9, feedback from the one or more sensors 5 is provided to the user and the user retains the user data temporarily for syncing with the cloud based system if an internet connection is not readily available, or lost. In an embodiment, medical sole system program 26 and/or the sole system program 18 updates the cloud based network server with pressure settings and GPS data, heart rate data, blood pressure data, and/or visual data collected during a user defined time period, from one or more components such as pressure sensors 5, and air chambers 9. In this example, a medical professional is able to access user data through either the web based service, or through medical sole system program 26 on computing device 27.

In an embodiment, sole system program 2 adjusts the pressure setting in one or more air chambers 9 and additionally provides navigational guidance to a user via GPS based on data received from the motion sensor and the captured visual sensor data. Navigation directions may be sent to the user via a computing device such as a phone, watch, tablet computer, or any other computing device known to one of ordinary skill in the art.

In another embodiment, medical sole system program 26, through a physical interface with wireless charging mat 22, automatically adjusts the pressure settings in one or more air chambers through an external attachment to air inlet 30, according to user preferences, and sends the data back to sole system 2. Alternatively, the adjustment of pressure settings can take place using the sole system program 18. For example, a user steps onto the wireless charging mat 22 and the user physically attaches an external pump, or compressor with a deflator to the sole system 2 via the external air inlet 30. In an embodiment, the external inlet 30 is connected to the chamber inlet/outlet 10*a*-10*h*. The medical sole system program 26 controls the amount of pressurized air provided to one or more air chambers via the external pump or compressor and/or the amount air depressurized from the one or more air chambers to achieve an optimal level according to user preferences. One of ordinary skill in the art understands that an optimal, or appropriate, pressure level is related to the level of comfort as determined by the settings of the user.

It should be noted that while the method was described relative to the medical professional, the user can alter the pressure settings in the one or more air chambers 9 of shoe via the sole system program 18.

It is to be understood that the embodiments of the present inventive concept herein described are merely illustrative of the application of the principles of the present inventive concept. References herein to details of the illustrated embodiments are not intended to limit the scope of the claims, which themselves recite those features regarded as essential to the present inventive concept.

What is claimed is:

1. A shoe sole having a forefoot, a heel and a medial arch connecting the forefoot to the heel, the shoe sole comprising:
    an insole containing at least three adjustable air chambers, wherein each of the at least three adjustable air chambers has a medial most point coincidental with a medial edge of the insole and a lateral most point coincidental with a lateral edge of the insole;
    an outsole having a top layer and a bottom layer, wherein the outsole further comprises:
    a) at least one processor compartment including a processor,
    b) a battery compartment including a battery;
    c) a first air pump compartment configured to provide air to a first adjustable air chamber of the at least three adjustable air chambers in the forefoot of the shoe sole;
    d) a second air pump compartment configured to provide air to a second adjustable air chamber of the at least three adjustable air chambers in the medial arch of the shoe sole; and
    e) a third air pump compartment configured to provide air to a third adjustable air chamber of the at least three adjustable air chambers in the heel of the shoe sole,
    wherein each of the first air pump compartment, the second air pump compartment and the third air pump compartment include an air pump with an inflator, deflator and pressure sensor; and
    a midsole located between the insole and the outsole, wherein the midsole contacts the insole and the top layer of the outsole.

2. The shoe sole of claim 1, wherein the outsole further comprises sensors selected from the group consisting of: a heart rate sensor, a blood pressure sensor, and a motion sensor.

3. The shoe sole of claim 1, wherein the first adjustable air chamber, the second adjustable air chamber and the third adjustable air chamber of the insole each further comprises an air inlet/outlet.

4. The shoe sole of claim 1, wherein the forefoot is at a first end of the shoe sole, the heel is at a second end of the shoe sole, and the medial arch is between the first end and the second end of the shoe sole, and wherein the first adjustable air chamber is a forefoot air chamber, the second adjustable air chamber is a medial arch air chamber, and the third adjustable air chamber is a heel air chamber.

5. The shoe sole of claim 4, wherein the forefoot air chamber has a pressure of 20 to 40 psi; the medial arch air chamber has a pressure of 20 to 40 psi; and the heel air chamber has a pressure of 30 to 50 psi.

6. The shoe sole of claim 1, wherein the at least three adjustable air chambers have a pressure level of range of 5 to 100 psi.

7. The shoe sole of claim 1, wherein the battery is a rechargeable battery and the shoe sole includes an indicator associated with a level of charge remaining in the rechargeable battery.

8. The shoe sole of claim 1, wherein the bottom layer of the outsole further comprises a metallic coil to charge the battery.

9. The shoe sole of claim 1, wherein the at least one processor is configured to wirelessly send data regarding each adjustable air chamber to a remote computing device.

10. The shoe sole of claim 9, wherein the at least one processor is configured to wirelessly send data via short range communication.

11. The shoe sole of claim 9, wherein the at least one processor is configured to wirelessly send data via long range communication.

* * * * *